United States Patent [19]

Zinnen

[11] Patent Number: 4,827,049

[45] Date of Patent: May 2, 1989

[54] PROCESS FOR THE SEPARATION OF DIHYDROXYBENZENE ISOMERS

[75] Inventor: Hermann A. Zinnen, Evanston, Ill.

[73] Assignee: UOP, Des Plaines, Ill.

[21] Appl. No.: 173,853

[22] Filed: Mar. 28, 1988

[51] Int. Cl.[4] .................. C07C 37/68; C07C 37/82
[52] U.S. Cl. .................................. 568/753; 568/750; 568/766
[58] Field of Search ............. 568/749, 750, 753, 751, 568/766; 570/211; 585/820

[56] References Cited

U.S. PATENT DOCUMENTS

| | | | |
|---|---|---|---|
| 2,985,589 | 5/1961 | Broughton et al. | 210/34 |
| 3,040,777 | 6/1962 | Carson et al. | 137/625.15 |
| 3,130,007 | 4/1964 | Breck | 23/113 |
| 3,422,848 | 1/1969 | Liebman et al. | 137/625.15 |
| 3,706,812 | 12/1972 | DeRosset et al. | 260/674 SA |
| 3,969,422 | 7/1976 | Neuzil et al. | 568/750 |
| 4,351,966 | 9/1982 | Flock | 568/753 |
| 4,356,331 | 10/1982 | Inoue et al. | 568/750 |
| 4,424,381 | 1/1984 | Leston | 568/753 |
| 4,571,441 | 2/1986 | Miwa et al. | 570/211 |
| 4,642,397 | 2/1987 | Zinnen et al. | 568/934 |

FOREIGN PATENT DOCUMENTS

| | | | |
|---|---|---|---|
| 0028017 | 2/1982 | Japan | 568/750 |
| 0031627 | 2/1982 | Japan | 570/211 |

OTHER PUBLICATIONS

Chem. Abstracts, CA105(14):121463y.
Chem. Abstracts, CA106(10):78001c.
Chem. Abstracts, CA72(3): 12227d.
T. Seki, J. Chromatogr. 115(1), 262-3.

Primary Examiner—Werren B. Lone
Attorney, Agent, or Firm—Thomas K. McBride; John F. Spears, Jr.; Jack H. Hall

[57] ABSTRACT

This invention comprises a process for separating isomers of dihydroxybenzene (DHB) from a feed mixture comprising at least two of said isomers, which process comprises contacting the mixture at adsorption conditions with an adsorbent comprising a Y type zeolite cation exchanged with a cation in the group Ca, Ba or Li, thereby selectively adsorbing o-DHB (catechol), or K, thereby selectively adsorbing p-DHB (hydroquinone). In the case where all three isomers are present in the feed, a cation from the first group is used, the remainder of the feed mixture is removed from the adsorbent and o-DHB is recovered by desorption at desorption conditions with methanol. P-DHB is recovered from the remainder by adsorption with the same or other adsorbent listed above and desorption at desorption conditions with ethanol.

10 Claims, 2 Drawing Sheets

PROCESS FOR THE SEPARATION OF DIHYDROXYBENZENE ISOMERS

BACKGROUND OF THE INVENTION

1. Field of the Invention

This invention pertains to the field of solid bed adsorptive separation of isomers of dihydroxybenzenes (DHB), viz. catechol (o-DHB), resorcinol (m-DHB) and hydroquinone (p-DHB), whose structural formulas are:

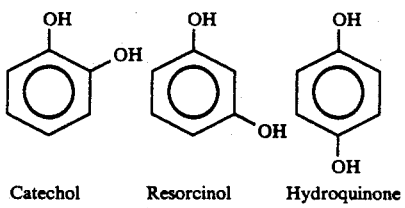

Catechol   Resorcinol   Hydroquinone

By a combined process, all three isomers can be recovered separately in high purity.

BACKGROUND INFORMATION

These valuable products are difficult to separate by conventional fractionation techniques, such as distillation, crystallization, sublimation, etc. Catechol is useful as antioxidants, light stabilizers, antiseptics, and dyestufffs, in photography, electroplating and printing applications. Resorcinol is used in the manufacture of pharmaceuticals, dyes, adhesives, etc. Hydroquinone has similar uses and also finds applications in textiles, paints, motor fuels and as polymerization inhibitors. Several publications have suggested possible adsorptive chromatographic processes for separating the isomers of dihydroxybenzene, but none have been successfully commercialized, to my knowledge. For example, silicalite, as a size selective adsorbent, was discussed in Chem. Abstracts, CA105(14):121463y; perfluoroamide-bonded silica gel was disclosed in Chem. Abstracts CA106(10):78001c; Merckogel PGM 2000 was disclosed by T. Seki, J. Chromatogr. 115(1), 262-3; graphitized carbon black was disclosed in Chem Abstracts CA72(3):12227d.

It is also known that crystalline aluminosilicates or zeolites are used in adsorption separations of various mixtures in the form of agglomerates having high physical strength and attrition resistance. Methods for forming the crystalline powders into such agglomerates include the addition of an inorganic binder, generally a clay comprising a silicon dioxide and aluminum oxide, to the high purity zeolite powder in wet mixture. The blended clay zeolite mixture is extruded into cylindrical type pellets or formed into beads which are subsequently calcined in order to convert the clay to an amorphous binder of considerable mechanical strength. As binders, clays of the kaolin type or silica are generally used. It is also known that water permeable organic polymers are superior binders.

The invention herein can be practiced in fixed or moving adsorbent bed systems, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Equipment utilizing these principles are familiar, in sizes ranging from pilot plant scale (deRossett U.S. Pat. No. 3,706,812) to commercial scale in flow rates from a few cc per hour to many thousands of gallons per hour.

The functions and properties of adsorbents and desorbents in the chromatographic separation of liquid components are well-known, but for reference thereto, Zinnen et al. U.S. Pat. No. 4,642,397 is incorporated herein.

I have discovered a process for employing specific zeolites for the separation of the isomers of dihydroxybenzene and, particularly, desorbents which are uniquely suitable for a combination process in which individual isomers are sequentially isolated from a feed mixture containing all three isomers.

SUMMARY OF THE INVENTION

It is, accordingly, a broad objective of the present invention to provide a process for the separation of each of the isomers of a feed mixture of dihydroxybenzene.

In brief summary, the process for separating one isomer from a feed mixture comprising at least two of the isomers comprises contacting, at adsorption conditions, the feed mixture with a type Y zeolite containing calcium, potassium, lithium or barium cations, selectively adsorbing the said one isomer onto the adsorbent to the substantial exclusion of the other isomer(s), removing the relatively non-adsorbed, i.e., less strongly adsorbed, isomers from contact with the adsorbent and thereafter recovering the selectively adsorbed isomer by desorption at desorption conditions with a desorbent material comprising methanol or ethanol.

To separate a feed mixture containing all three isomers, the process steps are repeated, using the same adsorbent, but different desorbents, in sequence, to separate and recover each of the isomers separately. In this combined process, catechol (o-DHB) is the most strongly adsorbed isomer on the preferred adsorbent, CaY, and is desorbed by methanol and recovered in the extract. The raffinate is again contacted with adsorbent and resorcinol (m-DHB) is recovered in the raffinate while hydroquinone (p-DHB) is desorbed with ethanol.

In an embodiment of the invention, o-DHB can be separated from mixtures with m-DHB or p-DHB using methanol as the desorbent. In another embodiment, p-DHB can be separated from mixtures with m-DHB, using ethanol as the desorbent.

Other objectives and embodiments of the present invention encompass details about feed mixtures, adsorbents, desorbent materials, operating conditions, etc., hereinafter disclosed.

DETAILED DESCRIPTION OF THE INVENTION

Figure 1:
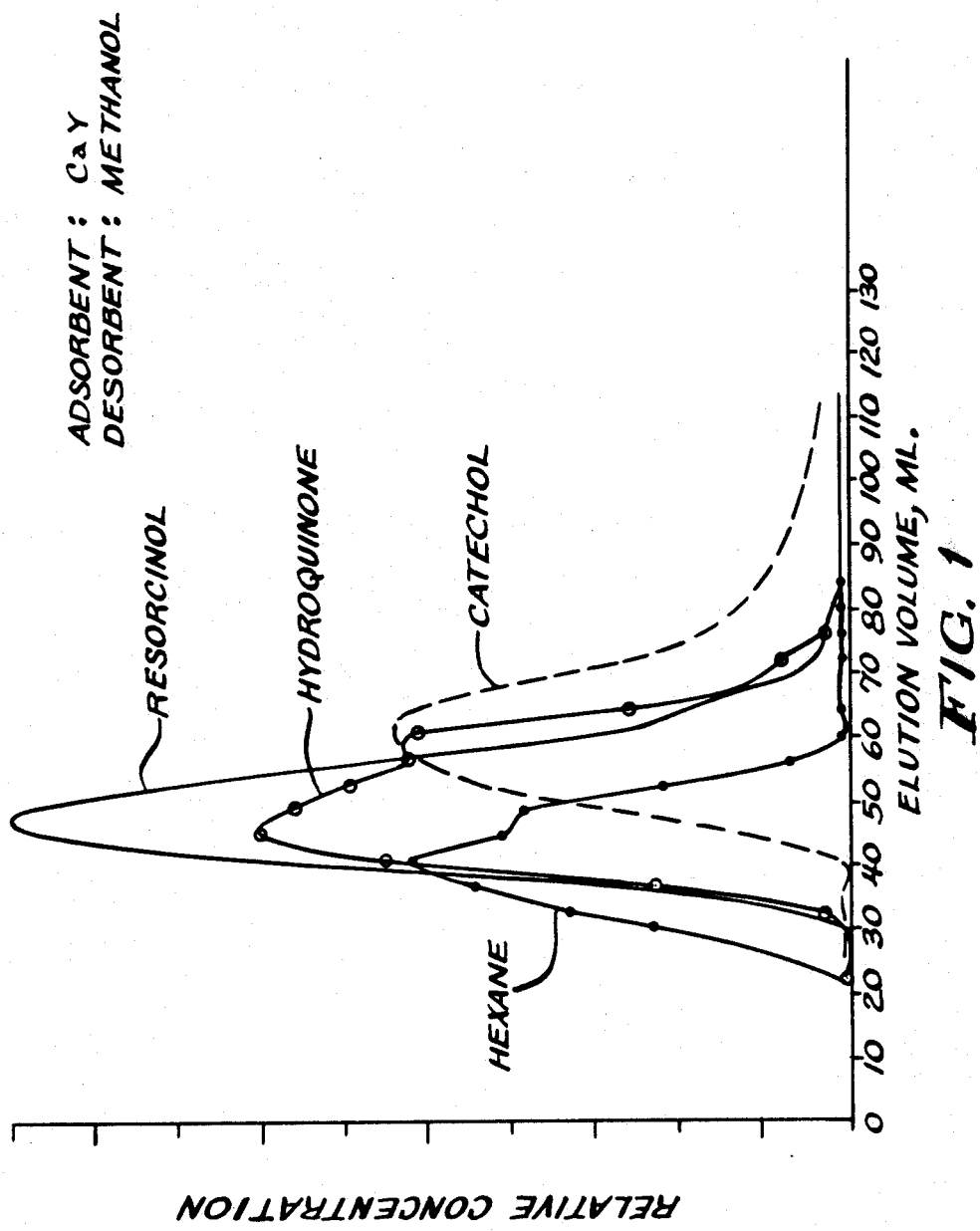
FIG. 1 is a graph of the pulse test of Example 2, showing the separation of catechol (o-DHB) from a feed mixture containing the three DHB isomers.

Adsorbents to be used in the process of this invention will comprise specific crystalline aluminosilicates or molecular sieves, namely Y zeolites. The zeolites have known cage structures in which the alumina and silica tetrahedra are intimately connected in an open three dimensional network to form cage-like structures with windowlike pores. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions and thus the crystalline aluminosilicates are often referred to as "molecular sieves."

In hydrated form, the Y zeolites used in the process of this invention have the structure described and defined in U.S. Pat. No. 3,130,007, incorporated herein by reference thereto, which can be represented in terms of moles of oxides by Formula 1 below:

Formula 1

$(0.9 \pm 0.2)M_{2/n}O:Al_2O_3:wSiO_2:yH_2O$ where "M" is at least one cation having a valence not more than 3, "n" represents the valence of "M", "w" is a value greater than about 3 up to about 6, and "y" is a value up to about 9 depending upon the identity of "M" and the degree of hydration of the crystal. The $SiO_2$/$Al_2O_3$ mole ratio for Y zeolites can thus be from about 3 to about 6. The cation "M", as the Y zeolite is initially prepared, is usually predominately sodium, but for the purpose of this invention, the sodium is replaced with calcium, barium, lithium or potassium cations by ion exchange methods well known to those having ordinary skill in the field of crystalline aluminosilicates. Such methods are generally performed by contacting the zeolite or an adsorbent material containing the zeolite with an aqueous solution of the soluble salt of the cation or cations desired to be placed upon the zeolite. After the desired degree of exchange takes place, the sieves are removed from the aqueous solution, washed, and dried to a desired water content.

The adsorbent may be supported by an inorganic matrix material such as silica, titania, or alumina or mixtures thereof, or compounds, such as clays, which material is present in intimate mixture with the small particles of the zeolite material. This matrix material, or binders, aids in forming or agglomerating the particles and may be an adjunct of the manufacturing process for zeolite,(for example, intentionally incomplete purification of the zeolite during its manufacture) or it may be added to relatively pure zeolite. Normally, the adsorbent will be in the form of particles such as extrudates, aggregates, tablets, macrospheres or granules having a desired particle size range. The typical adsorbent will have a particle size range of about 16-60 mesh (Standard U.S. Mesh).

In this process, and particularly the preferred continuous simulated moving bed process, the desorbent must be selected to satisfy the following criteria: First, the desorbent material should displace an extract component from the adsorbent with reasonable mass flow rates without itself being so strongly adsorbed as to unduly prevent an extract component from displacing the desorbent material in a following adsorption cycle. Secondly, the desorbent material must be compatible with the particular adsorbent and the particular feed mixture. More specifically, it must not reduce or destroy the critical selectivity of the adsorbent for an extract component with respect to a raffinate component or react chemically with the feed components. The desorbent should additionally be easily separable from the feed mixture that is passed into the process. Both the raffinate stream and the extract stream are removed from the adsorbent in admixture with desorbent material and without a method of separating at least a portion of the desorbent material, the purity of the extract product and the raffinate product would not be very high nor would the desorbent material be available for reuse in the process. It is therefore contemplated that any desorbent material used in this process will preferably have a substantially different average boiling point than that of the feed mixture, i.e., more than about 5° C. difference, to allow separation of at least a portion of desorbent material from feed components in the extract and raffinate streams by simple fractional distillation, thereby permitting reuse of desorbent material in the process. Finally, desorbent materials should also be materials which are readily available and therefore reasonable in cost. However, a suitable desorbent or desorbents for a particular separation with a specific adsorbent are not always predictable. In the preferred isothermal, isobaric, liquid-phase operation of the process of my invention, I have found that desorbent material comprising methanol or ethanol will result in selectivity for a particular adsorbed DHB isomer when used with the above discussed adsorbents. Certain combinations of adsorbent and desorbent were found to be most effective in separating the DHB isomers depending on the composition of the feed mixture to be separated.

When the feed mixture contains all three DHB isomers, to separate the isomers, it is necessary to proceed in two stages: First, the feed mixture is contacted with, preferably a Ca-exchanged Y zeolite. M- and p-DHB are removed in the raffinate and the more strongly adsorbed isomer, o-DHB, is desorbed with methanol and recovered as extract. Second, the raffinate from the first stage is contacted with the same adsorbent, which may be exchanged with the same cation and purified m-DHB is recovered as raffinate. Hydroquinone (p-DHB) is desorbed with ethanol. Ethanol is not strong enough to desorb o-DHB rapidly, and therefore is not particularly efficient when used in the first stage of this combined process. On the other hand, while methanol is somewhat selective between m- and p-DHB as will be seen from Example II in which the selectivity of m- to p-DHB is only 1.36, it is preferred to use ethanol in the second stage, which yields greater selectivity and gives better resolution.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Adsorption conditions will include a temperature range of from about 20° to about 200° C. with about 20° to about 100° C. being more preferred and a pressure sufficient to maintain liquid phase, ranging from about atmospheric to about 500 psig with from about atmospheric to about 25 psig being preferred. Desorption conditions will include the same range of temperatures and pressures as used for adsorption conditions.

At least a portion of the extract stream, and preferably at least a portion of the raffinate stream, from the separation process are passed to separation means, typically fractionators or evaporators, where at least a portion of desorbent material is separated to produce an extract product and a raffinate product, respectively.

A static test procedure and apparatus may be employed to test various adsorbents with a particular feed mixture to determine the relative retention by the adsorbent of each component of the mixture. The procedure involves mixing together equal quantities of each component, the relative retention of which is to be determined, and a convenient solvent or desorbent material. The resulting solution is then placed in a vessel with a quantity of the appropriate adsorbent and is allowed to remain, with occasional stirring, for about 24 hours. The solution is then analyzed for each component and the relative retention thereof is determined in terms of the ratio, R, of the less strongly adsorbed component to the more strongly adsorbed component, the relative retention of the more strongly adsorbed component by the adsorbent being greater, the higher the above ratio.

A dynamic testing apparatus is employed to test various adsorbents with a particular feed mixture and desorbent material to measure the adsorption characteristics of retention capacity and exchange rate. The apparatus consists of a helical adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect qualitatively or determine quantitatively one or more components in the effluent stream leaving the adsorbent chamber. A pulse test, performed using this apparatus and the following general procedure, is used to determine the data, e.g., selectivity, for various adsorbent systems. The adsorbent is placed in a chamber and filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent material is injected for a duration of several minutes. Desorbent material flow is resumed, and the tracer and the extract component or the raffinate component (or both) are eluted as in a liquid-solid chromatographic operation. The effluent can be analyzed on-stream or alternatively, effluent samples can be collected periodically and later analyzed separately by analytical equipment and traces of the envelopes or corresponding component peaks developed.

From information derived from the test, adsorbent performance can be rated in terms of void volume, retention volume for an extract or a raffinate component, and the rate of desorption of an extract component from the adsorbent and selectivity. Void volume is the nonselective volume of the adsorbent, which is expressed by the amount of desorbent pumped during the interval from initial flow to the center of the peak envelope of the tracer. The retention volume (net) of an extract or a raffinate component may be characterized by the distance between the center of the peak envelope of the extract or raffinate component and the center of the peak envelope of the tracer component or some other known reference point. It is expressed in terms of the volume in cubic centimeters of desorbent material pumped during this time interval represented by the distance between the peak envelopes. The rate of exchange or desorption rate of an extract component with the desorbent material can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is again the volume of desorbent material pumped during this time interval. Selectivity, $\beta$, is determined by the ratio of the net retention volumes of the more strongly adsorbed component to each of the other components.

The following non-limiting examples are presented to illustrate the process of the present invention and are not intended to unduly restrict the scope of the claims attached hereto.

EXAMPLE I

A number of static tests were performed as described hereinabove at 25° C. to demonstrate that it was possible to separate the isomers by an adsorptive process. Stock solutions of dihydroxybenzene (DHB) isomers as follows were used in the tests:

|  | Stock Solution 1 | Stock Solution 2 |
|---|---|---|
| o-DHB (catechol) | 1.95 g | — |
| p-DHB (hydroquinone) | 1.95 g | 0.97 g |
| m-DHB (resorcinol) | — | 0.97 g |
| n-pentanol | 68 g | 34 g |

In the static tests, the volume ratio of stock solution to adsorbent was 2. Each stock solution and adsorbent were combined in a flask and the amount of each isomer left in the raffinate was determined and the isomer ratios $R_{C/H}$ and $R_{R/H}$, (C=catechol, H=hydroquinone, R=resorcinol) were calculated for a number of adsorbents. The results are as follows:

TABLE 1

| Absorbent | $R_{C/H}$ of Feed Solution 1 | $R_{C/H}$ of Raffinate | Adsorbed DHB Isomer |
|---|---|---|---|
| Ba—Y | 1.0 | 0.512 | o-DHB |
| Ca—Y | 1.0 | 0.495 | o-DHB |
| K—Y | 1.0 | 1.46 | p-DHB |
| Li | 1.0 | 0.649 | o-DHB |
| | $R_{R/H}$ of Feed Solution 2 | $R_{R/H}$ of Raffinate | |
| Ba—Y | 1.0 | 1.35 | p-DHB |
| Ca—Y | 1.0 | 1.25 | p-DHB |
| K—Y | 1.0 | 1.29 | p-DHB |
| Li | 1.0 | 1.49 | p-DHB |

These tests show that o-DHB is more strongly adsorbed than p-DHB by Ba-, Ca-, and Li-exchanged Y zeolite and less strongly adsorbed by K-Y zeolite. Further, p-DHB is more strongly adsorbed than m-DHB by all these adsorbents. Hence, in combination with an appropriate desorbent, methanol or ethanol, determined as stated above, these isomers may be separated by our adsorptive process. The preferred adsorbent, Ca-Y, also underwent the pulse test as described in the next example, confirming the results of the static test.

EXAMPLE II

The previously described pulse test was used to obtain data for this example, which illustrates the separation of o-DHB from a feed mixture comprising all three DHB isomers and the first stage of the combined process for separating all the individual isomers. The liquid temperature was 100° C. and the flow was up the column at the rate of 1.2 ml/min. The feed stream comprised 2.6 cc pulses of a solution containing 0.5 g of each of the dihydroxybenzene isomers, 0.5 g of n-hexane tracer and 2 cc methanol. The column was packed with clay bound calcium-exchanged Y zeolite adsorbent of 30-60 mesh particle size. The desorbent was 100% methanol.

The selectivity ($\beta$), as earlier described, was calculated from the trace of the peaks generated for the components. The results of this example are shown on the following Table 2 and FIG. 1:

TABLE 2

| Isomer | Gross Retention Volume (cc) | Net Retention Volume (NRV) (cc) | Selectivity, $\beta$* |
|---|---|---|---|
| m-DHB | 47.6 | 6.6 | C/H = 2.11 |
| o-DHB | 60.0 | 19.0 | C/R = 2.87 |
| p-DHB | 50.0 | 9.0 | H/R = 1.36 |
| n-Hexane | 41.0 | 0 | |

*C = catechol, R = resorcinol, H = hydroquinone

EXAMPLE III

Figure 2:
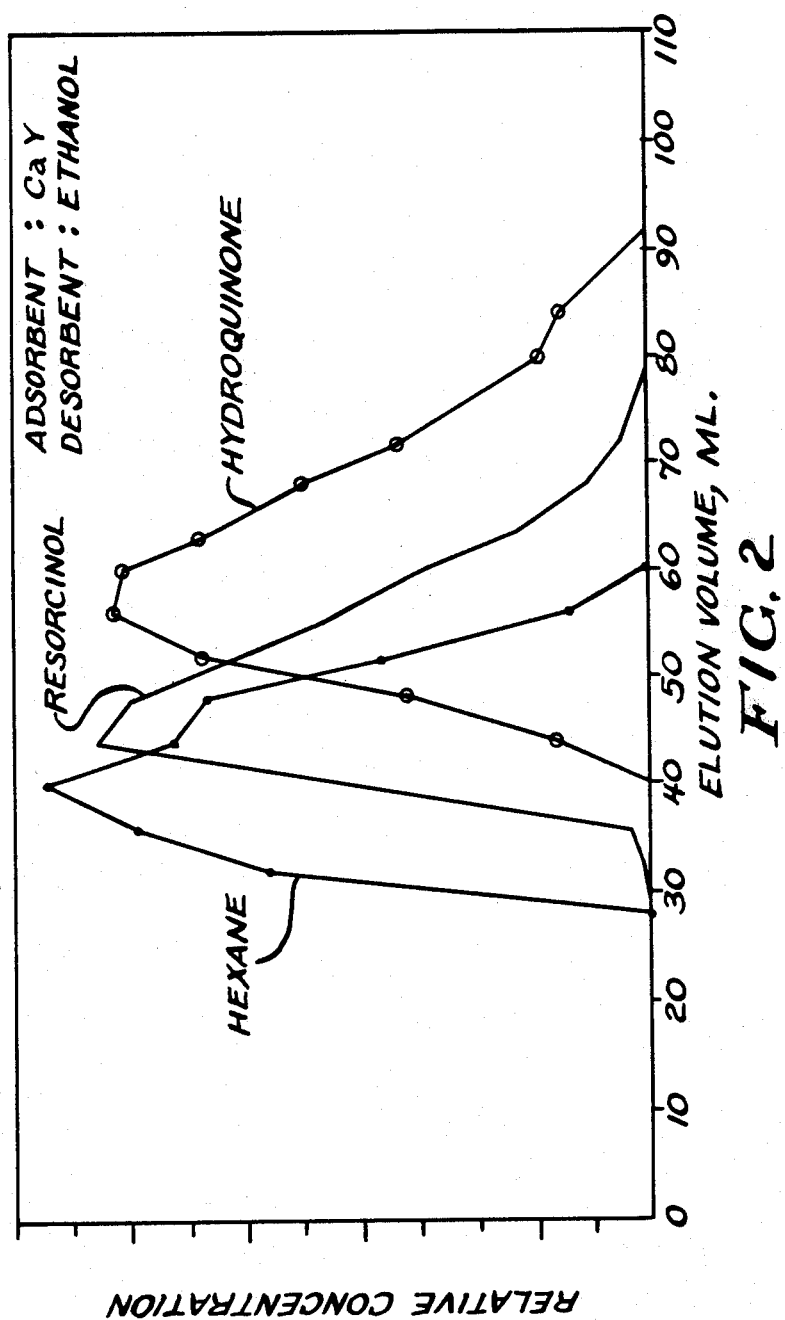
FIG. 2 is a graph of the pulse test of Example 3, showing the separation of a feed mixture containing m-DHB and p-DHB, e.g., from the raffinate obtained from the separation of Example 2.

The previously described pulse test was also used to obtain data to illustrate the separation of m- and p-DHB and the second stage of the combined process where the first stage raffinate, containing m- and p-DHB, is separated into its components. In this example, a normal hexane tracer, ethanol desorbent and a calcium-exchanged Y-type zeolite adsorbent were used. In these tests, the column temperature was 117° C., flow rate up the column was 1.2 cc per minute and a feed stream pulse of 2.6 cc containing 0.5 g each of resorcinol, hydroquinone and n-hexane, and 2 cc ethanol was used. Hydroquinone (p-DHB) is selectively adsorbed. The resuls of the pulse test are shown in FIG. 2 and Table 2 below:

TABLE 3

| Isomer | Gross Retention Volume (cc) | Net Retention Volume (NRV) (cc) | Selectivity, $\beta$* |
|---|---|---|---|
| m-DHB (R) | 49.0 | 8.0 | H/R = 2.37 |
| p-DHB (H) | 60.0 | 19.0 | |

TABLE 3-continued

| Isomer | Gross Retention Volume (cc) | Net Retention Volume (NRV) (cc) | Selectivity, $\beta$* |
|---|---|---|---|
| n-Hexane | 41.0 | 0 | |

*R = resorcinol, H = hydroquinone

I claim:

1. A process for separating a dihydroxybenzene isomer from a feed mixture comprising at least two dihydroxybenzene isomers, said process comprising contacting said mixture at adsorption conditions within the range of from about 20° to about 200° C. and a pressure sufficient to maintain liquid phase with an adsorbent comprising a Y type zeolite, cation exchanged with a ction from the Group K, Ca, Ba and Li thereby selectively adsorbing one of said isomers, removing the remainder of said mixture from said adsorbent, and then recovering said adsorbed isomer by desorption at desorption conditions within the range of from about 20° to about 200° C. and a pressure sufficient to maintain liquid phase with a desorbent material comprising ethanol or methanol.

2. The process of claim 1 wherein said process is effected with a simulated moving bed flow system.

3. The process of claim 1 wherein said adsorbent is a Y type zeolite whose cations have been exchanged with calcium.

4. The process of claim 3 wherein said desorbent is methanol and said selectively adsorbed isomer is o-dihydroxybenzene.

5. The process of claim 4 wherein said feed mixture comprises o-, m- and p-dihydroxybenzene.

6. The process of claim 1 wherein said desorbent is ethanol and said selectively adsorbed isomer is p-dihydroxybenzene.

7. The process of claim 6 wherein said adsorbent is calcium-exchanged.

8. The process of claim 5 wherein a mixture of m- and p-dihydroxybenzene are recovered in said remainder, contacting said remainder with a Y zeolite adsorbent exchanged with a cation exchanged with a cation selected from the group consisting of K, Ca, Ba and Li thereby selectively adsorbing said p-dihydroxybenzene, removing said m-dihydroxybenzene from said adsorbent and then recovering said p-dihydroxybenzene by desorption at desorption conditions with ethanol.

9. The process of claim 8 wherein said adsorbent is exchanged with calcium ions.

10. The process of claim 1 wherein said feed mixture comprises m- and p-hydroxybenzene, said adsorbent is Ca-exchanged, said adsorbed isomer is p-dihydroxybenzene and said desorbent is ethanol.

* * * * *

UNITED STATES PATENT AND TRADEMARK OFFICE
CERTIFICATE OF CORRECTION

PATENT NO. : 4,827,049
DATED : May 2, 1989
INVENTOR(S) : HERMANN A. ZINNEN

It is certified that error appears in the above-identified patent and that said Letters Patent is hereby corrected as shown below:

In Column 8, line 43: Delete "exchanged with a cation" (second occurrence).

Signed and Sealed this

Sixteenth Day of January, 1990

Attest:

JEFFREY M. SAMUELS

Attesting Officer     Acting Commissioner of Patents and Trademarks